United States Patent
Fritzinger et al.

(10) Patent No.: US 10,265,112 B2
(45) Date of Patent: Apr. 23, 2019

(54) CLAVICLE BENDING TEMPLATES

(71) Applicant: Biomet Manufacturing, LLC, Warsaw, IN (US)

(72) Inventors: Daniel D. Fritzinger, Warsaw, IN (US); Robert J. Taylor, Elkhart, IN (US)

(73) Assignee: Biomet Manufacturing, LLC, Warsaw, IN (US)

(*) Notice: Subject to any disclaimer, the term of this patent is extended or adjusted under 35 U.S.C. 154(b) by 664 days.

(21) Appl. No.: 14/749,689

(22) Filed: Jun. 25, 2015

(65) Prior Publication Data

US 2016/0374742 A1 Dec. 29, 2016
US 2017/0100181 A9 Apr. 13, 2017

Related U.S. Application Data

(62) Division of application No. 13/342,672, filed on Jan. 3, 2012, now Pat. No. 9,072,556.

(51) Int. Cl.
  *A61B 17/88* (2006.01)
  *A61B 17/80* (2006.01)
  *A61B 50/00* (2016.01)

(52) U.S. Cl.
  CPC ...... *A61B 17/8863* (2013.01); *A61B 17/8057* (2013.01); *A61B 17/8061* (2013.01); *A61B 17/8085* (2013.01); *A61B 17/808* (2013.01); *A61B 2050/005* (2016.02)

(58) Field of Classification Search
  CPC .............. A61B 17/808; A61B 17/8085; A61B 17/8863; A61F 2/0095
  See application file for complete search history.

(56) References Cited

U.S. PATENT DOCUMENTS

| | | |
|---|---|---|
| 3,866,458 A | 2/1975 | Wagner |
| 5,113,685 A | 5/1992 | Asher et al. |
| 5,651,283 A | 7/1997 | Runciman et al. |
| 5,746,742 A | 5/1998 | Runciman et al. |
| 6,978,188 B1 | 12/2005 | Christensen |
| 7,740,634 B2 | 6/2010 | Orbay et al. |
| 9,072,556 B2 | 7/2015 | Fritzinger et al. |
| 2003/0055435 A1 | 3/2003 | Barrick et al. |
| 2006/0085000 A1* | 4/2006 | Mohr ............... A61B 17/8076 606/281 |
| 2007/0083204 A1 | 4/2007 | Sidebotham |

(Continued)

FOREIGN PATENT DOCUMENTS

RU 2387398 C1 4/2010

OTHER PUBLICATIONS

U.S. Appl. No. 13/342,674 U.S. Pat. No. 9,072,556, filed Jan. 3, 2012, Clavicle Bending Templates.

(Continued)

*Primary Examiner* — Andrew Yang
(74) *Attorney, Agent, or Firm* — Schwegman Lundberg & Woessner, P.A.

(57) ABSTRACT

A reference guide tool for conforming a bone plate can include a series of bone templates, each having a distinct three-dimensional shape that replicates portions of various clavicles. Each bone template of the series of bone templates can have a plate engaging surface that is configured to engage a bone plate and provide a reference for the bone plates during structural modification of the bone plate.

8 Claims, 4 Drawing Sheets

(56) References Cited

U.S. PATENT DOCUMENTS

2009/0306724 A1* 12/2009 Leither .............. A61B 17/8057
606/289
2013/0172948 A1 7/2013 Fritzinger et al.
2013/0304074 A1* 11/2013 Knoepfle ........... A61B 17/8863
606/101

OTHER PUBLICATIONS

"U.S. Appl. No. 13/342,672, Non Final Office Action dated Nov. 5, 2014", 10 pgs.
"U.S. Appl. No. 13/342,672, Notice of Allowance dated Mar. 2, 2015", 8 pgs.
"U.S. Appl. No. 13/342,672, Response filed Jan. 30, 2015 to Non Final Office Action dated Nov. 5, 2014", 10 pgs.
"U.S. Appl. No. 13/342,672, Response filed Oct. 13, 2014 to Restriction Requirement dated Aug. 29, 2014", 6 pgs.
"U.S. Appl. No. 13/342,672, Restriction Requirement dated Aug. 29, 2014", 9 pgs.
"SPS Small Fragment Set", Stryker Trauma, AG, (2007), 20 pgs.

\* cited by examiner

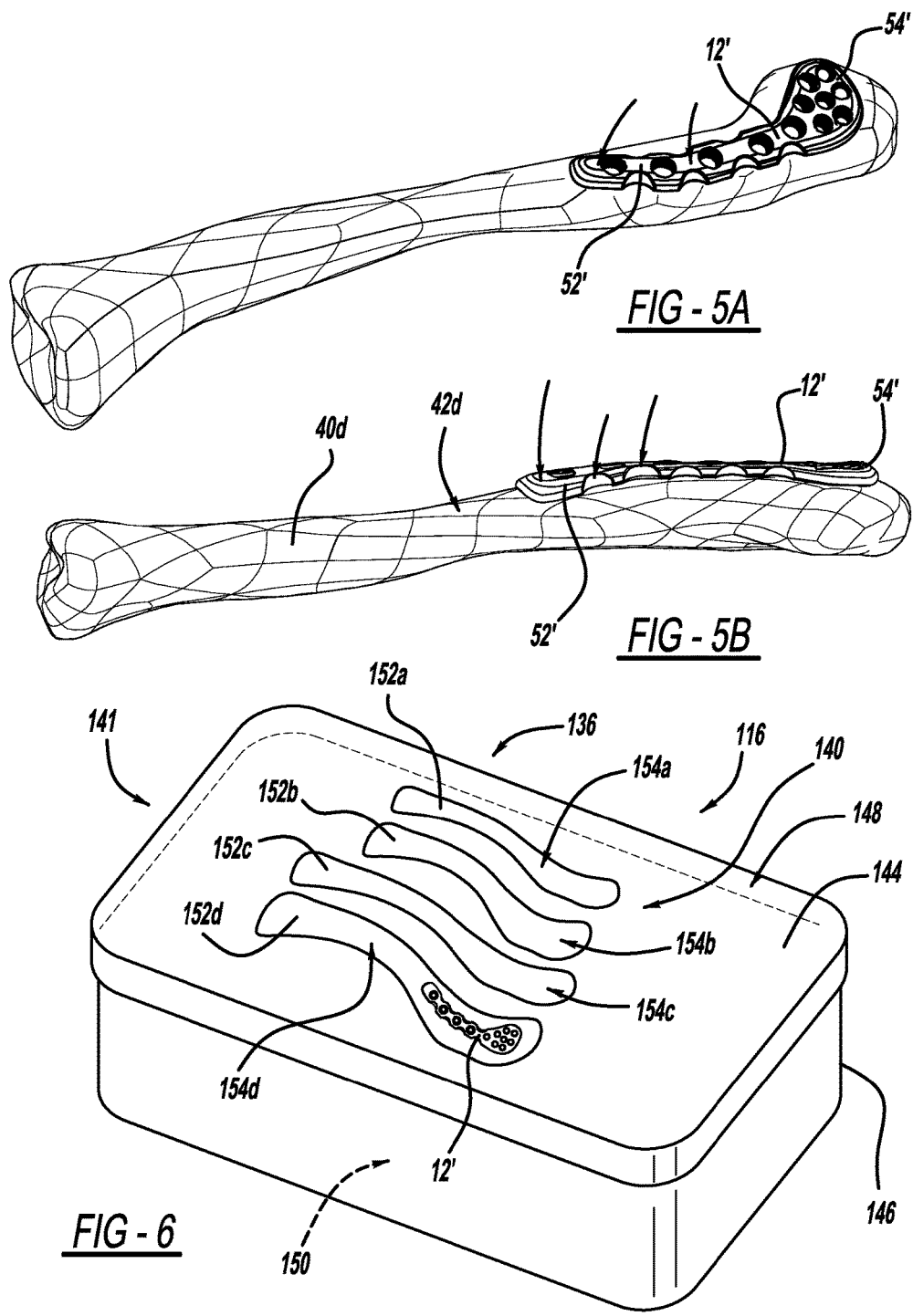

CLAVICLE BENDING TEMPLATES

CROSS-REFERENCE TO RELATED APPLICATIONS

This application is a divisional of U.S. patent application Ser. No. 13/342,672 filed on 3 Jan. 2012. The entire disclosure of the above application is incorporated herein by reference.

FIELD

The present disclosure relates generally to bone fixation and more particularly, to a reference guide tool and related methods for conforming a bone plate to a profile suitable to implant against a fractured bone.

BACKGROUND

This section provides background information related to the present disclosure which is not necessarily prior art.

Portions of the anatomy can generally be formed relative to one another to allow for a natural articulation, support, movement, or the like. Nevertheless, due to various circumstances, such as injury, disease, or the like, various portions of the anatomy can become damaged. In various orthopedic surgical procedures, it may be necessary to align and secure fractured bone portions in a relatively fixed relationship to each other. For example, it may be necessary to establish such a secured relationship after the bone has been fractured. To ensure that the bone can regenerate in the proper orientation and fuse the fracture, it may be important that the bone portions be fixed relative to each other.

It is known in the art to provide metal plates for the repair of bone fractures. The plates may be generally secured to the fractured bone portions with fasteners such as bone screws. In the case of a clavicle fracture, it may be particularly challenging to provide a bone plate that specifically matches the profile of the patient's clavicle. In this regard, the clavicle generally includes an "S" shape in a superior-inferior view. The sharpness of the curves that form the "S" as well as the overall length of the clavicle varies greatly across a large patient population. Therefore, it is often necessary for a surgeon to specifically structurally modify the contour of a given plate to match the clavicle of the particular patient.

According to one common technique, a surgeon may bend a bone plate in the operating room to fit a particular patient's broken bone. Usually, the bending is a trial and error process. The surgeon may place the bone plate onto the fractured bone, determine where the bend in the plate is desired, take the plate off of the bone, bend the plate and then place the plate back on the patient's bone to verify fit. The process may be repeated until adequate fit is achieved. As can be appreciated, the process may be particularly lengthy for highly contoured bones such as a clavicle resulting in a prolonged surgery.

SUMMARY

This section provides a general summary of the disclosure, and is not a comprehensive disclosure of its full scope or all of its features.

A reference guide tool for conforming a bone plate can include a series of bone templates, each having a distinct three-dimensional shape that replicates portions of various clavicles. Each bone template of the series of bone templates can have a plate engaging surface that is configured to engage a bone plate and provide a reference for the bone plates during structural modification of the bone plate.

According to additional features, the reference guide tool further comprises a base that collectively retains the series of bone templates. The base can collectively retain the series of bone templates statically relative to each other. The series of bone templates can extend proud from the base. The respective plate engaging surfaces of the bone templates extend proud from the base. According to some examples, the plate engaging surfaces can correspond to a superior surface of the various clavicles. According to other features, the plate engaging surfaces can further correspond to an anterior surface of the various clavicles. The base can comprise a lid for a case. According to other features, the reference guide tool can further comprise a case that is configured to receive the lid and collectively define an interior space with the lid. In one example, the series of bone templates and the base can be monolithically formed.

A method for forming a bone plate for implantation against a clavicle can include determining a geometry of the clavicle. A corresponding bone template from a series of bone templates can be selected based on the determined geometry of the clavicle. Each bone template of the series of bone templates can have a distinct three-dimensional shape that replicates portions of various clavicles. Each bone template of the series of bone templates can have a plate engaging surface that is configured to engage a bone plate. A bone plate can be selected. The bone plate can be placed against the plate engaging surface. The bone plate can be structurally modified while referencing the plate engaging surface of the selected bone template. The structurally modified bone plate can be implanted onto a clavicle of the patient.

According to additional features, structurally modifying the bone plate can comprise forming the bone plate against the plate engaging surface. The plate engaging surface can correspond to at least one of a superior and anterior surface of the clavicle. According to other features, determining the geometry of the clavicle can comprise referencing a medical image of the clavicle.

The method according to the present disclosure can further comprise placing the structurally modified bone plate against the clavicle. A determination is made whether a satisfactory engagement between the bone plate and the clavicle has been attained. Further structural modifications on the bone plate can be performed based on the determination. According to other features, the method can further comprise autoclaving a base that is collectively formed with the series of bone templates as a unitary piece.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 5A is a posterior perspective view of the bone template of FIG. 4B and shown with initial deflection of the bone plate in a generally superior-inferior direction to match the profile of the bone template;

FIG. 5B is another posterior perspective view of the bone template of FIG. 5A and shown subsequent to further deflection of the bone plate in the superior-inferior direction;

Figure 1:
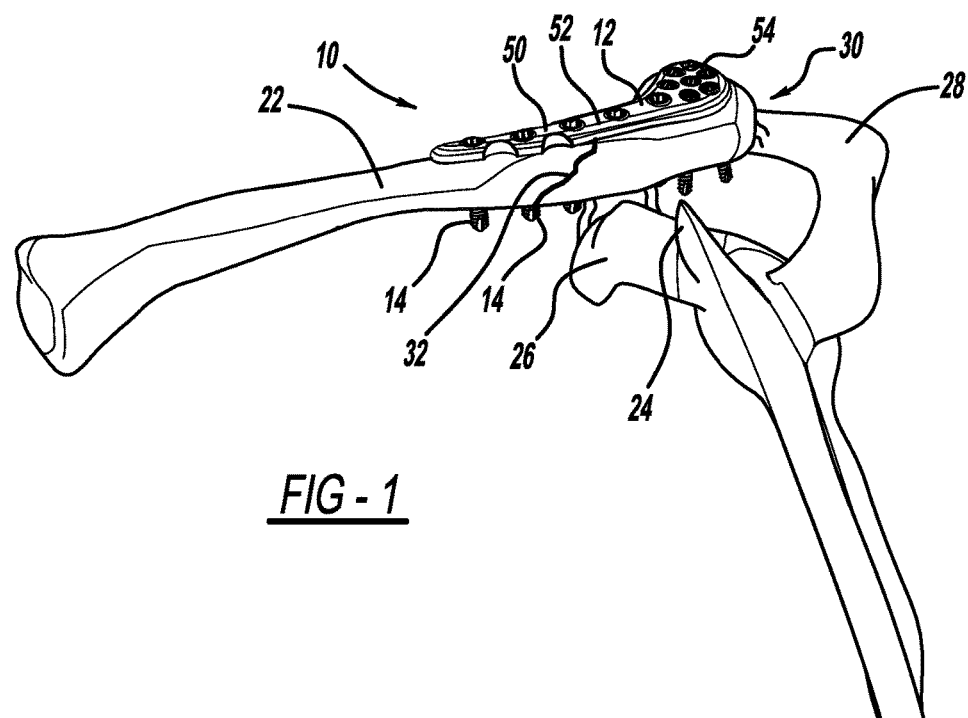
FIG. 1 is a posterior perspective view of a bone plate shown in an implanted position relative to a right clavicle and scapula of a patient subsequent to structurally modifying the bone plate while referencing a reference guide tool according to the present disclosure.
Figure 7:
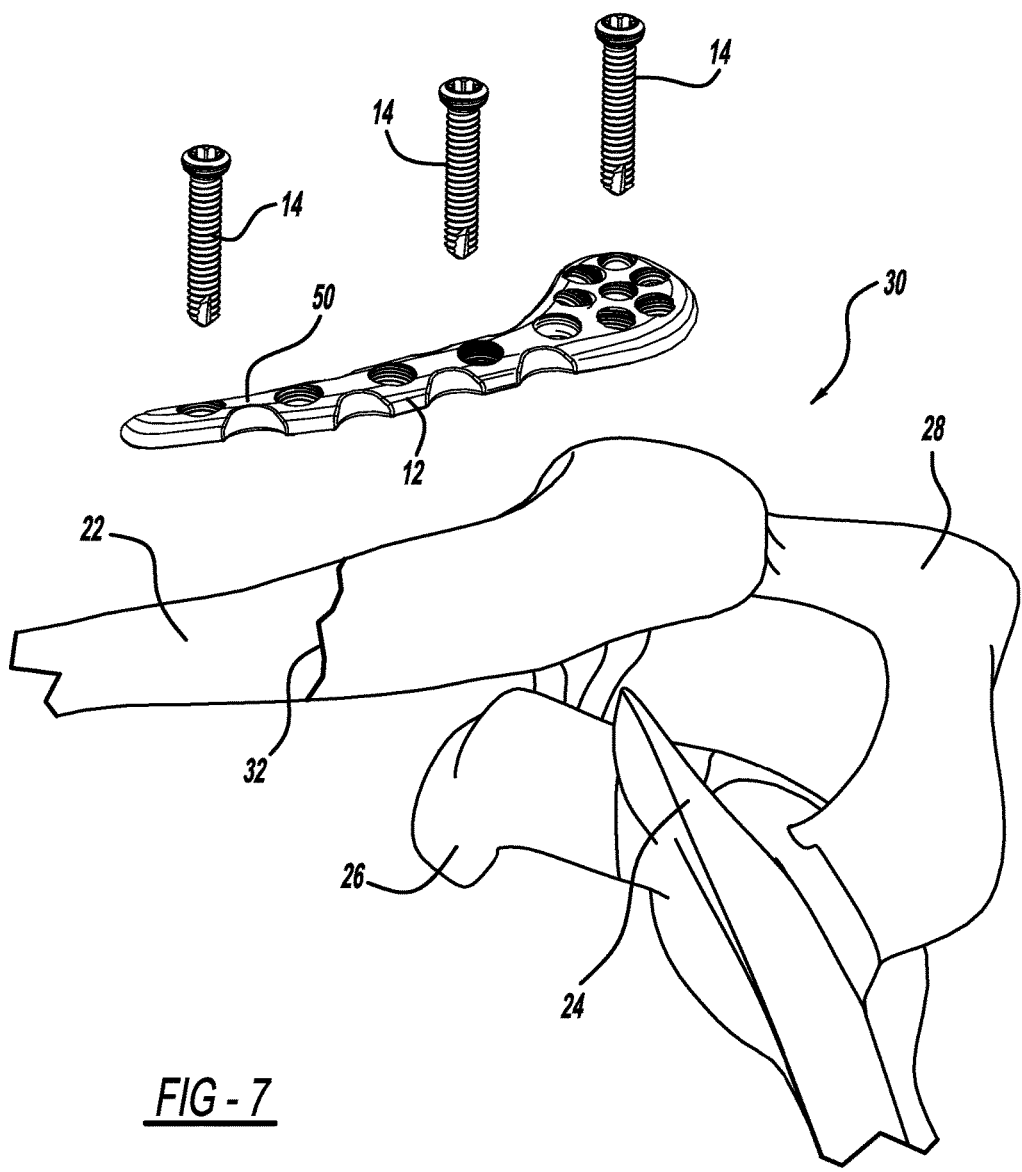

FIG. 6 is a top perspective view of a base in the form of a lid that includes the first, second, third, and fourth bone templates integrally formed thereon according to additional features of the present disclosure and shown as part of a surgical container that further comprises a box; and FIG. 7 is a posterior perspective view of the right clavicle and scapula of the patient shown in FIG. 1 and illustrated with the structurally deformed bone plate and exemplary fasteners in exploded view prior to implantation.

Corresponding reference numerals indicate corresponding parts throughout the several views of the drawings.

DETAILED DESCRIPTION

Example embodiments will now be described more fully with reference to the accompanying drawings.

The following description of the various embodiments is merely exemplary in nature and is in no way intended to limit the teachings, their application or uses. While the following description is directed toward a reference guide tool that is specifically configured for forming bone plates relative to a right clavicle, it will be appreciated that the same may be applied to forming bone plates relative to a left clavicle. Furthermore, while the following discussion is specifically directed toward bone plates that are structurally deformed to fit on clavicle bones, the same may be applied to other long bones.

With initial reference to FIG. 1, a bone plate assembly 10 is shown in an implanted position. The bone plate assembly 10 can generally include a structurally deformed bone plate 12 and a series of bone screws 14. As will become appreciated from the following discussion, the structurally deformed bone plate 12 can be conformed to a desired shape prior to implantation using the reference guide tool 16 (FIG. 2) and related techniques discussed herein. Briefly, a patient's anatomy can include a clavicle 22 and a scapula 24 having a coracoid process 26 and acromion 28. The clavicle 22 and acromion 28 can cooperate to form an articulating portion such as the acromioclavicular joint 30. The clavicle 22 is illustrated having a fracture 32. The bone plate assembly 10 according to the present teachings, once implanted, can generally fix the clavicle 22 back to a desired position such that any unfavorable deflection of the clavicle 22 can be minimized.

Figure 2:
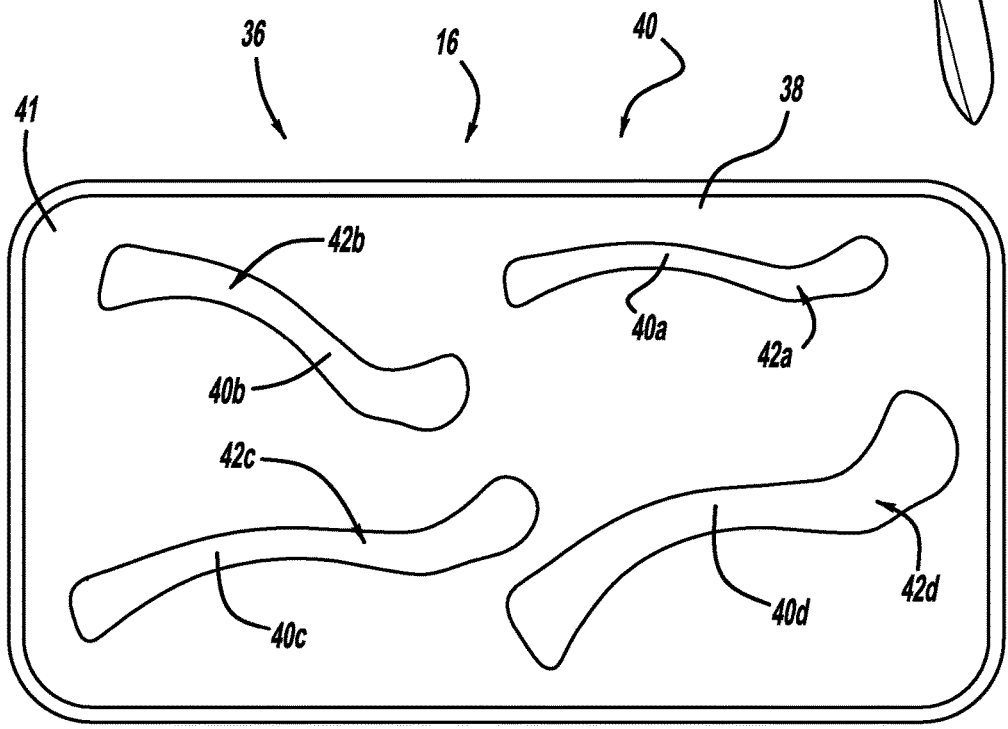
FIG. 2 is a top view of a reference guide tool including a series of bone templates, each having a distinct three-dimensional shape according to the present teachings.

With specific reference now to FIG. 2, the reference guide tool 16 according to one example of the present teachings will be described in greater detail. The reference guide tool 16 can generally include a bone template kit 36 having a base or tray 38 that includes a series of bone templates 40. The base or tray 38 may be part of a case 41 that can further include an enclosure for capturing the series of bone templates 40.

The series of bone templates 40 as shown generally includes a first bone template 40a, a second bone template 40b, a third bone template 40c, and a fourth bone template 40d. In the example shown, the series of bone templates 40 replicates right clavicles having different sizes. It will be appreciated that the series of bone templates 40 can additionally or alternatively include left clavicles having different sizes. Moreover, additional bone templates having other sizes may be included. Specifically, each bone template 40a, 40b, 40c, and 40d has a distinct three-dimensional shape that replicates portions of various clavicles.

The first bone template 40a can generally include a plate engaging surface 42a. The second bone template 40b can generally include a plate engaging surface 42b. The third bone template 40c can generally include a plate engaging surface 42c. The fourth bone template 40d can generally include a plate engaging surface 42d. As will be appreciated from the following discussion, each bone template of the series of bone templates 40 can replicate the geometry of various clavicles. The surgeon can determine which bone template of the series of bone templates 40 most accurately represents the clavicle 22 of the patient. The determination may be made before surgery such as by viewing medical imaging information and/or intraoperatively by examining the subject clavicle.

As will be described herein more fully, the surgeon can take a bone plate 12 and mechanically deflect and/or deform the bone plate around the bone template (40a, 40b, 40c, or 40d) to form and reshape the bone plate 12 into a geometry that is best suited for receipt against the clavicle 22 of the patient. As can be appreciated, the surgeon can reference the three-dimensional shape of the selected bone template 40a, 40b, 40c, or 40d and make any necessary deformations on the bone plate 12 while engaging the respective plate engaging surface 42a, 42b, 42c, or 42d instead of needing to engage and/or reference the actual clavicle 22 during the forming the shape of the bone plate 12. The deflecting and forming of the bone plate 12 may be accomplished by any means such as by hand and/or by instruments.

Figure 3:
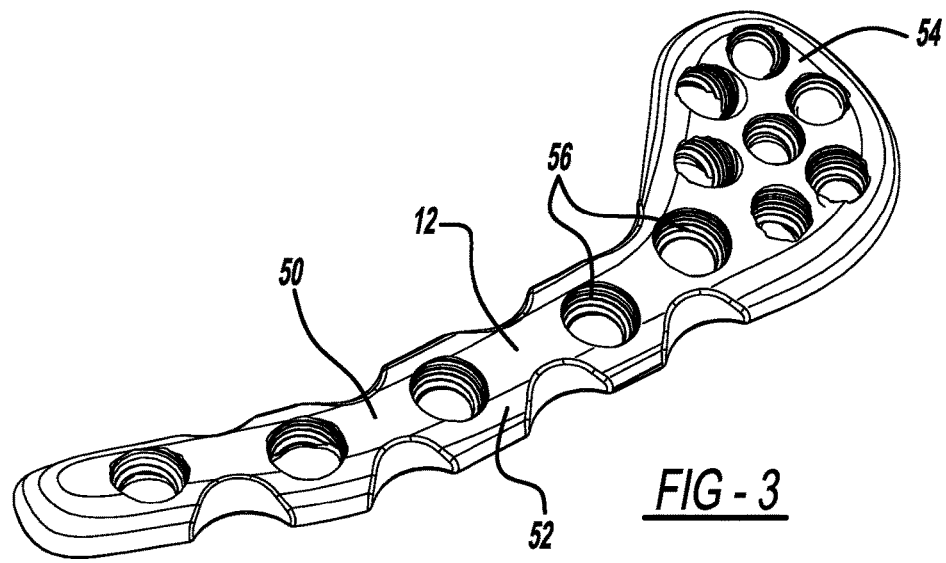
FIG. 3 is a front perspective view of the bone plate of FIG. 1.

With reference now to FIGS. 3-5B, an exemplary method of forming the bone plate 12 to match the geometrical profile of a selected bone template will be described in greater detail. The bone plate 12, while shown as having a particular shape, may have other shapes and sizes as desired for the needs of a particular patient. As such, the reference guide tool 16 can be used to aid a surgeon in shaping bone plates of any size and shape. A brief description of the exemplary bone plate 12 will now be described. The bone plate 12 can be formed of biocompatible metal and generally include a bone plate body 50 that generally includes an elongated body portion 52 and a platform portion 54. A plurality of threaded apertures 56 may be formed through the body 50. The bone plate 12 illustrated in FIG. 3 represents a geometry subsequent to shaping using the reference guide tool 16.

Figure 4A:
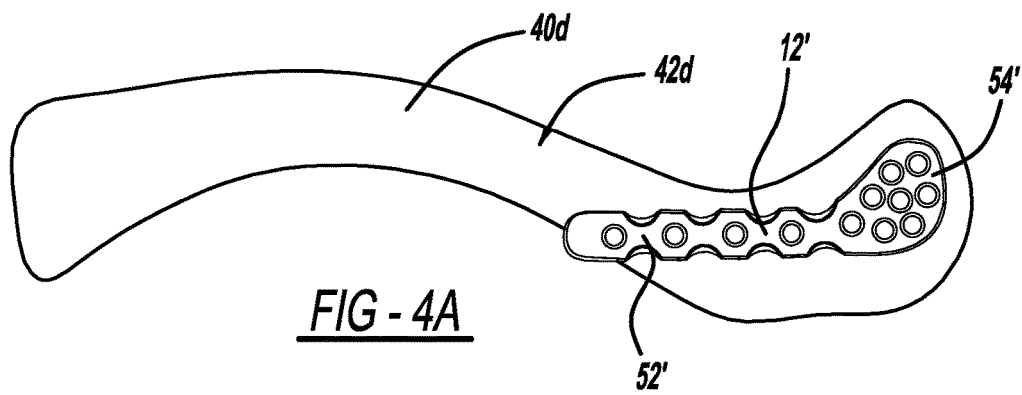
FIG. 4A is a superior view of the fourth bone template of the bone templates shown in FIG. 2 having an unmodified bone plate positioned against a superior surface of the bone template.
Figure 4B:
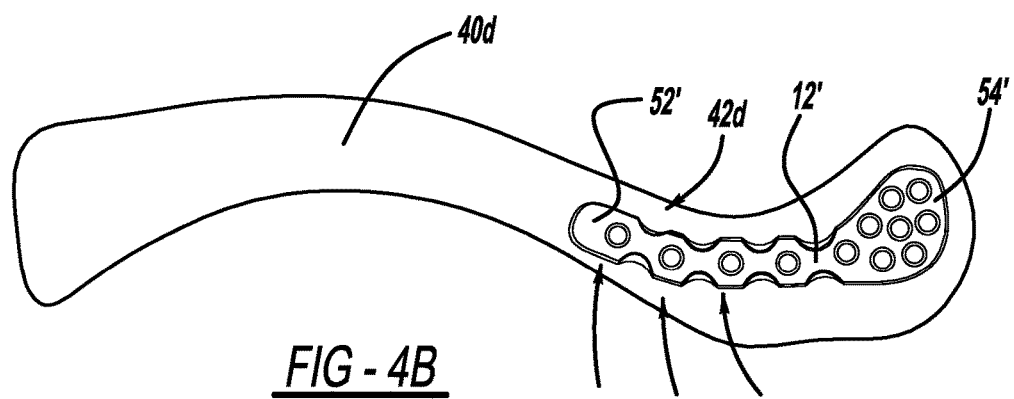
FIG. 4B is a superior view of the fourth bone template shown in FIG. 4A and shown during structured modification of a portion of the bone plate in an anterior-posterior direction to match the profile of the bone template.

With specific reference now to FIG. 4A, a bone plate 12' is illustrated positioned against the bone plate engaging surface 42d of the bone template 40d. The "prime" suffix of the bone plate 12' is used to denote a bone plate that has been selected as a preferred size and prior to deforming it to match the profile of the bone template 40d. Turning now to FIG. 4B, a surgeon can bend the bone plate 12' such as at an elongated body portion 52'. In the example shown, the bone plate 12' is formed generally posteriorly to better match the profile of the plate engaging surface 42d of the bone template 40d. It will be appreciated that the surgeon be cognizant of minimizing deflection in areas that may compromise the geometry of the threaded apertures 56 that are anticipated to be used to receive the bone screws 14.

With further reference to FIGS. 5A and 5B, the bone plate 12' is shown further deflected in a generally inferior direction against the bone plate engaging surface 42d of the bone template 40d. It is appreciated that the surgeon can additionally or alternatively deform the bone plate 12' such as by twisting the bone plate 12' along its elongated axis. In this regard, the bone plate 12' can be manipulated in many directions until a desired coverage is attained against the bone plate engaging surface 42d of the bone template 40d.

Once a desired contour has been attained on the bone plate 12, the bone plate 12 can be positioned against the clavicle 22 of the patient to verify whether an adequate coverage or fit can be attained. In some examples, it may be necessary to further deflect/manipulate the bone plate 12 to achieve a desired profile. Once an adequate fit has been achieved, the surgeon can advance the bone screws 14 through selected threaded apertures 56 of the bone plate 12. It will be appreciated that the advancement of the bone screws 14 can further bring the bone plate 12 to match the geometry of the clavicle 22.

Turning now to FIG. 6, a reference guide tool 116 constructed in accordance to additional features of the present disclosure will be described. The reference guide tool 116 can generally comprise a bone template kit 136 having a series of bone templates 140. The bone template kit 136 can generally include a case 141 having a base 144 that can cooperate with an enclosure 146. In the example shown, the base 144 is in the form of a lid 148 that cooperates with the enclosure 146 to define an interior space 150. The base 144 can include a first, second, third, and fourth bone template 152a, 152b, 152c, and 152d formed thereon.

In the example shown in FIG. 6, the reference guide tool 116 incorporates the series of bone templates 140 onto the base 144. In the example shown, the base 144, or lid 148 incorporates the first, second, third, and fourth bone templates 152a, 152b, 152c, and 152d in a configuration so as to extend proud from the lid 148 as a single piece. In some examples, the series of bone templates 140 can be formed directly into the lid as a monolithic piece. The first bone template 152a includes a bone plate engaging surface 154a. The second bone template 152b incorporates a bone plate engaging surface 154b. The third bone template 152c incorporates a bone plate engaging surface 154c. The fourth bone template 152d incorporates a bone plate engaging surface 154d. The respective bone plate engaging surfaces 154a, 154b, 154c and 154d can generally include the superior, anterior, and posterior surfaces of a clavicle. In this regard, a surgeon can have easy access to the surfaces of a clavicle that typically are identified for receipt of a bone plate during clavicle fixation. Additionally, because the series of bone templates 140 are formed onto the lid 148, a surgeon may stabilize the bone templates 140 during the forming of the bone plate 12 simply by holding a portion of the lid 148.

As with the reference guide tool 16 described above, the reference guide tool 116 allows a surgeon to initially determine which bone template most accurately represents the clavicle 22 of the given patient. Once the desired bone template has been selected that most closely matches the clavicle 22 of the patient, a surgeon can directly engage a bone plate 12' (such as the fourth bone template 152d) and mechanically deform the bone plate 12' against the bone plate engaging surface 154d of the fourth bone template 152d until the desired geometrical profile has been attained. Next, the surgeon can take the deformed bone plate 12' and position it against the clavicle 22 to verify whether the desired profile has been attained. Again, in some examples, the surgeon may need to further manipulate the shape of the bone plate prior to implanting onto the clavicle 22.

Turning now to FIG. 7, once the bone plate 12 has been manipulated to the desired geometrical profile using the reference guide tool 16 or 116, the bone plate 12 may be secured to the clavicle 22 with the bone screws 14. According to another advantage of the reference guide tool 116, the bone templates 140 can be sterilized (autoclaved, etc.) simply by sterilizing the base 144 (or, in the example shown, the lid 148). In this regard, the need to account for multiple loose components is minimized.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A reference guide tool for conforming a bone plate comprising:
   a series of bone templates having corresponding distinct three-dimensional shapes that replicate portions of various clavicles, wherein each bone template of the series of bone templates has a plate engaging surface configured to engage a bone plate and provide a reference for the bone plate during structural modification of the bone plate, wherein the plate engaging surfaces correspond to a superior surface, an anterior surface, and a posterior surface of the various clavicles;
   a base that collectively retains the series of bone templates, wherein the base collectively retains the series of bone templates statically relative to each other wherein the series of bone templates extend proud from the base; and
   wherein the respective plate engaging surfaces of the bone templates extend proud from the base, and wherein the bone templates are formed on the base such that the bone templates and the base are a monolithic single piece.

2. A reference guide tool for conforming a bone plate comprising:
   a series of bone templates having corresponding distinct three-dimensional shapes that replicate portions of various clavicles; and
   a base that collectively secures each bone template of the series of bone templates in a fixed position relative to each other, wherein each bone template of the series of bone templates has a plate engaging surface configured to engage a bone plate and provide a reference for the bone plate during structural modification of the bone plate;
   wherein the series of bone templates are monolithically formed on the base such that the bone templates and the base are a monolithic single piece and the base collectively retains the series of bone templates statically relative to each other, and wherein the series of bone templates extend proud from the base.

3. The reference guide tool of claim 2, wherein the plate engaging surfaces correspond to at least one of a superior and anterior surface of the various clavicles.

4. The reference guide tool of claim 2, wherein the base comprises a lid for a case.

5. The reference guide tool of claim 4, wherein the case is configured to receive the lid and collectively define an interior space with the lid.

6. The reference guide tool of claim 2, in combination with the plate.

7. The reference guide tool of claim 2, wherein the base is an autoclaved base.

8. The reference guide tool of claim 2, wherein the base is constructed of a material suitable for autoclaving.

* * * * *